United States Patent

Papay

(10) Patent No.: US 9,204,925 B2
(45) Date of Patent: Dec. 8, 2015

(54) APPARATUS AND METHOD FOR TREATING A NEUROMUSCULAR DEFECT

(71) Applicant: Francis A. Papay, Westlake, OH (US)

(72) Inventor: Francis A. Papay, Westlake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/788,322

(22) Filed: Mar. 7, 2013

(65) Prior Publication Data

US 2013/0281967 A1 Oct. 24, 2013

Related U.S. Application Data

(63) Continuation-in-part of application No. 12/541,221, filed on Aug. 14, 2009, now Pat. No. 8,512,715.

(60) Provisional application No. 61/089,015, filed on Aug. 14, 2008.

(51) Int. Cl.
| | |
|---|---|
| *A61B 18/18* | (2006.01) |
| *A61B 18/14* | (2006.01) |
| *A61M 5/20* | (2006.01) |
| *A61B 18/00* | (2006.01) |

(52) U.S. Cl.
CPC ... *A61B 18/1477* (2013.01); *A61B 2018/00434* (2013.01); *A61B 2018/00452* (2013.01); *A61B 2018/00577* (2013.01); *A61B 2018/00839* (2013.01); *A61B 2218/007* (2013.01); *A61M 5/20* (2013.01)

(58) Field of Classification Search
CPC ....................................... A61B 18/18
See application file for complete search history.

(56) References Cited

U.S. PATENT DOCUMENTS

| | | | | |
|---|---|---|---|---|
| 4,512,349 A | * | 4/1985 | Hunt et al. | 600/360 |
| 4,928,690 A | * | 5/1990 | Heilman et al. | 607/4 |
| 4,943,290 A | * | 7/1990 | Rexroth et al. | 606/45 |
| 5,336,172 A | * | 8/1994 | Bales et al. | 604/27 |
| 5,354,291 A | * | 10/1994 | Bales et al. | 604/35 |
| 5,449,357 A | * | 9/1995 | Zinnanti | 606/49 |

(Continued)

FOREIGN PATENT DOCUMENTS

| | | |
|---|---|---|
| WO | 9426186 A1 | 11/1994 |
| WO | 0112089 A1 | 2/2001 |
| WO | 2008039188 A1 | 4/2008 |

OTHER PUBLICATIONS

PCT International Search Report and Written Opinion, mailed Nov. 6, 2013, pp. 1-9.

(Continued)

*Primary Examiner* — Albert Navarro
*Assistant Examiner* — Ginny Portner
(74) *Attorney, Agent, or Firm* — Tarolli, Sundheim, Covell & Tummino LLP (57) ABSTRACT

One aspect of the present disclosure relates to a treatment probe comprising an elongated body member and a needle portion. The elongated body member can have a proximal end portion and a distal end portion. The needle portion can be connected to the distal end portion. The needle portion can include at least one electrode and at least one fluid port. The at least one electrode and the at least one fluid port can be configured to deliver electrical energy and a tumescent fluid, respectively, so that superficial tissue planes overlying a target nerve are protected from inadvertent heat damage as a result of application of electrical energy to a target nerve.

12 Claims, 11 Drawing Sheets

(56) References Cited

U.S. PATENT DOCUMENTS

| | | | |
|---|---|---|---|
| 5,674,235 A * | 10/1997 | Parisi | 606/169 |
| 5,714,468 A | 2/1998 | Binder | |
| 5,800,420 A * | 9/1998 | Gross et al. | 604/890.1 |
| 5,860,957 A * | 1/1999 | Jacobsen et al. | 604/156 |
| 6,102,885 A * | 8/2000 | Bass | 604/22 |
| 6,139,545 A | 10/2000 | Utley et al. | |
| 6,171,238 B1 * | 1/2001 | Klimes et al. | 600/345 |
| 6,221,056 B1 * | 4/2001 | Silverman | 604/239 |
| 6,485,436 B1 * | 11/2002 | Truckai et al. | 600/564 |
| 6,491,690 B1 * | 12/2002 | Goble et al. | 606/41 |
| 6,896,886 B2 | 5/2005 | Aoki et al. | |
| 7,632,266 B2 * | 12/2009 | Scopton et al. | 606/41 |
| 7,713,266 B2 * | 5/2010 | Elkins et al. | 606/21 |
| 7,862,563 B1 * | 1/2011 | Cosman et al. | 606/41 |
| 7,947,039 B2 * | 5/2011 | Sartor | 606/42 |
| 8,182,444 B2 * | 5/2012 | Uber et al. | 604/66 |
| 8,317,771 B2 * | 11/2012 | Mitelberg et al. | 604/506 |
| 8,721,632 B2 * | 5/2014 | Hoey et al. | 606/27 |
| 2001/0032001 A1 | 10/2001 | Ricart et al. | |
| 2002/0002372 A1 * | 1/2002 | Jahns et al. | 606/41 |
| 2003/0216724 A1 * | 11/2003 | Jahns | 606/41 |
| 2004/0102770 A1 * | 5/2004 | Goble | 606/34 |
| 2005/0070844 A1 * | 3/2005 | Chow et al. | 604/95.04 |
| 2005/0084504 A1 | 4/2005 | Aoki et al. | |
| 2005/0183732 A1 * | 8/2005 | Edwards | 128/898 |
| 2005/0209564 A1 * | 9/2005 | Bonner et al. | 604/173 |
| 2005/0215945 A1 * | 9/2005 | Harris et al. | 604/66 |
| 2005/0224086 A1 * | 10/2005 | Nahon | 128/899 |
| 2005/0240147 A1 * | 10/2005 | Makower et al. | 604/96.01 |
| 2006/0041243 A1 * | 2/2006 | Nayak et al. | 604/506 |
| 2006/0079873 A1 * | 4/2006 | Scopton et al. | 606/37 |
| 2007/0129714 A1 | 6/2007 | Elkins et al. | |
| 2007/0167943 A1 | 7/2007 | Janssen et al. | |
| 2007/0255342 A1 | 11/2007 | Laufer | |
| 2007/0258906 A1 * | 11/2007 | Fischman et al. | 424/9.71 |
| 2008/0009747 A1 * | 1/2008 | Saadat et al. | 600/471 |
| 2008/0069841 A1 | 3/2008 | Panjwani et al. | |
| 2008/0154254 A1 * | 6/2008 | Burger et al. | 606/23 |
| 2008/0183164 A1 * | 7/2008 | Elkins et al. | 606/21 |
| 2009/0138025 A1 * | 5/2009 | Stahler et al. | 606/130 |
| 2009/0192522 A1 * | 7/2009 | Blumenkranz | 606/130 |
| 2009/0312617 A1 * | 12/2009 | Creed et al. | 600/345 |
| 2010/0114095 A1 | 5/2010 | Janssen et al. | |
| 2011/0202056 A1 * | 8/2011 | Sartor | 606/42 |
| 2012/0059286 A1 * | 3/2012 | Hastings et al. | 601/2 |
| 2013/0310823 A1 * | 11/2013 | Gelfand et al. | 606/33 |
| 2014/0276539 A1 * | 9/2014 | Allison et al. | 604/500 |
| 2014/0343542 A1 * | 11/2014 | Karnik et al. | 606/24 |
| 2014/0343543 A1 * | 11/2014 | Karnik et al. | 606/24 |

OTHER PUBLICATIONS

Barwood et al., "Analgesic Effects of Botulinum Toxin A: A Randomized, Placebo-controlled Clinical Trial", Developmental Medicine & Child Neurology, 2000, vol. 42, pp. 116-121.

Ferrante et al., "The Analgesic Response to Intravenous Lidocaine in the Treatment of Neuropathic Pain", Anesthesia & Analgesia, 1996, vol. 82 pp. 91-97.

* cited by examiner

APPARATUS AND METHOD FOR TREATING A NEUROMUSCULAR DEFECT

RELATED APPLICATIONS

This application is a continuation-in-part of U.S. patent application Ser. No. 12/541,221, filed Aug. 14, 2009, which claims priority from U.S. Provisional Patent Application Ser. No. 61/089,015, filed Aug. 14, 2008. The subject matter of each of the aforementioned applications is hereby incorporated by reference in its entirety.

TECHNICAL FIELD

The present disclosure relates generally to an apparatus and method for neuromodulation, and more particularly to an apparatus and method for interrupting nerve conduction through a target nerve to treat a neuromuscular defect.

BACKGROUND

The human nervous system senses current information and conditions, which it then sends to various muscles to respond. As one example, consider the facial and neck nerves. These motor nerves control the muscles of facial expression and, thus, an individual's outward manifestations of well being and emotion. Neuromuscular defects can disrupt this information exchange and lead to undesired muscle responses.

The involuntary contraction of facial or neck muscles (also known as dystonias) can distort an individual's facial expressions and garble the outward appearance of the individual's feeling of well being and emotional state. For example, one type of dystonia, called belpharospasm, creates uncontrolled blinking and spasms in the eyelids. Another form of dystonia causes uncontrolled grimacing. Dystonias can also affect neck muscles. For example, one form of dystonia, called torticollis, causes uncontrolled contraction of the neck muscles.

Apart from these hyperfunctional disorders, normal contraction of facial and neck muscles (e.g., by frowning or squinting) can form permanent furrows or bands in the skin over time. These furrows or bands can present an aesthetically displeasing cosmetic appearance, and exposure to the sun can accelerate this undesired wrinkling process. As a more specific example, the facial muscle corrugator supercilii draws the eyebrows downward and inward, producing vertical wrinkles of the forehead (also called glabellar frown lines). For this reason, the corrugator supercilii is known as the frowning muscle and has been called the principal agent in the expression of suffering. Dystonias affecting the corrugator supercilii can lead to an unfortunate, continuous frowning expression, as well as the formation of hyperfunctional frown lines and wrinkles in the face.

A surgical forehead lift procedure is one therapeutic modality often used to remove glabellar frown lines. The forehead lift requires a large incision that extends from ear to ear over the top of the forehead. This surgically invasive procedure imposes the risk of bleeding and creates a large skin flap that reduces blood supply to the skin. Numbness of sensory nerves in the face, such as the supraorbital nerve can also result.

A less invasive therapeutic modality is the administration of invertebrate exotoxins. For example, injection of the serotype A of the Botulinum toxin produces a flaccid paralysis of the corrugator supercilii. Tests have demonstrated that Botulinum toxin A may be administered into the musculature of the face without toxic effect to produce localized muscle relaxation for a period of about six months. The desired removal of hyperfunctional frowning lines is temporary, and repeated treatments are needed about every 3 to 6 months.

Another form of treatment, disclosed in U.S. Pat. No. 5,370,642 to Keller, uses laser energy to eliminate glabellar frown lines and forehead wrinkles. The laser energy is used to resect large sections of the corrugator supercilii (as well as other facial muscles) and thereby inactivate the muscles. Like the surgical forehead lift, numbness of the supraorbital nerve and other sensory nerves in the face can result.

SUMMARY

One aspect of the present disclosure relates to a treatment probe comprising an elongated body member and a needle portion. The elongated body member can have a proximal end portion and a distal end portion. The needle portion can be connected to the distal end portion. The needle portion can include at least one electrode and at least one fluid port. The at least one electrode and the at least one fluid port can be configured to deliver electrical energy and a tumescent fluid, respectively, so that superficial tissue planes overlying a target nerve are protected from inadvertent heat damage as a result of application of electrical energy to a target nerve.

Another aspect of the present disclosure relates to a method for treating a neuromuscular defect in a subject. One step of the method can comprise providing a treatment probe. The treatment probe can include a body member having a proximal end portion, a distal end portion, and a needle portion connected to the distal end portion. The needle portion can include at least one electrode and at least one fluid port that is oppositely disposed from the at least one electrode. Next, the needle portion can be positioned about a target nerve. A tumescent fluid can then be injected into the tissue surrounding the target nerve via the at least one fluid port. An electric current can be delivered to the at least one electrode to substantially ablate the target nerve.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "modulate" or "modulating" can refer to causing a change in neuronal activity, chemistry, and/or metabolism. The change can refer to an increase, decrease, or even a change in a pattern of neuronal activity. The terms may refer to either excitatory or inhibitory stimulation, or a combination thereof, and may be at least electrical, magnetic, thermal, ultrasonic, optical or chemical, or a combination of two or more of these. The terms "modulate" or "modulating" can also be used to refer to a masking, altering, or overriding of neuronal activity.

Figure 8:
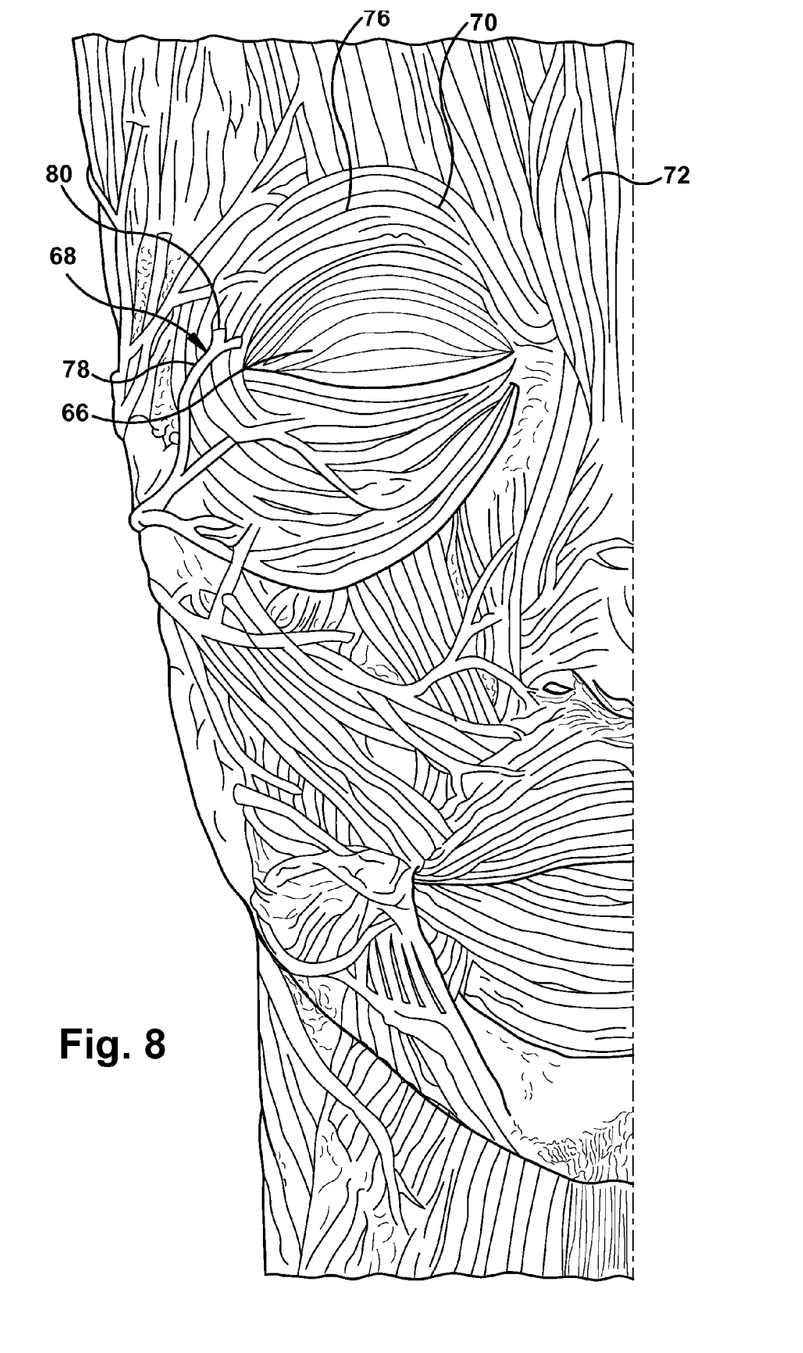
FIG. 8 is an anterior view of the right side of the face showing the superficial facial and neck muscles and the branches of the facial nerves that control the facial and neck muscles.

As used herein, the term "target nerve" can refer to any portion of a human (or other mammalian) nervous system that has been identified to benefit from receiving electric current. Non-limiting examples of target nerves can include the facial nerve and any one of its branches, such as the temporal branch, the zygomatic branch, the buccal branch, the marginal mandibular branch, and the cervical branch. Other examples of target nerves are illustrated in FIG. 8 and described in more detail below.

As used herein, the term "substantially ablate" can refer to damage caused to a target nerve that results in partial or complete nervous tissue or nerve cell necrosis. The term can also refer to nervous tissue or nerve cell damage that falls short of complete ablation, e.g., some level of agitation or damage that is imparted to the nervous tissue or nerve cell to inure a desired change in the cellular makeup and/or electrical activity of the tissue/cell, rather than necrosis of the tissue/cell.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "substantially blocked" or "substantially block" when used with reference to activity at or associated with a target nerve target can refer to a complete (e.g., 100%) or partial inhibition (e.g., less than 100%, such as about 90%, about 80%, about 70%, about 60%, or less than about 50%) of nerve conduction through the target nerve.

As used herein, the term "activity" when used with reference to a target nerve can, in some instances, refer to the ability of a target nerve to conduct, propagate, and/or generate an action potential. In other instances, the term can refer to the frequency at which a target nerve is conducting, propagating, and/or generating one or more action potentials at a given moment in time. In further instances, the term can refer to the frequency at which a target nerve is conducting, propagating, and/or generating one or more action potentials over a given period of time (e.g., seconds, minutes, hours, days, etc.).

As used herein, the term "electrical communication" can refer to the ability of an electric field generated by an electrode or electrode array to be transferred, or to have a neuromodulatory effect, within and/or on a target nerve.

As used herein, the terms "treat" or "treating" can refer to therapeutically regulating, preventing, improving, alleviating the symptoms of, and/or reducing the effects of a neuromuscular defect. As such, treatment also includes situations where a neuromuscular defect, or at least symptoms associated therewith, is completely inhibited, e.g., prevented from happening or stopped (e.g., terminated) such that the subject no longer suffers from the neuromuscular defect, or at least the symptoms that characterize the neuromuscular defect.

As used herein, the terms "neuromuscular defect" or "neuromuscular junction disorder" can refer to abnormal or dysfunctional communication between a nerve and a muscle.

Overview

The present disclosure relates generally to an apparatus and method for neuromodulation, and more particularly to an apparatus and method for interrupting nerve conduction through a target nerve to treat a neuromuscular defect. Conventional nerve ablation procedures, such as those used to ablate peripheral nerves using RF energy, can be effective in inhibiting unwanted muscle contraction and movement. Due to the relatively shallow anatomical location of such nerves, however, delivery of ablation energy often causes undesirable damage to tissues surrounding the ablated nerve(s). Advantageously, the present disclosure provides apparatus and methods for protecting superficial tissue planes from inadvertent heat damage during nerve ablation procedures, thereby reducing or preventing unwanted scarring and disruption of neighboring nerves and/or blood vessels. As described in more detail below, the present disclosure can be used to treat a variety of neuromuscular defects and/or neuromuscular junction disorders, such as cosmetic conditions affecting the face and neck, as well as headaches and neuromuscular pain.

Apparatus

One aspect of the present disclosure includes a treatment probe 10 (FIG. 1) comprising an elongated body member 12 and a needle portion 14. The elongated body member 12 can include an ergonomically-shaped housing having a proximal end portion 16, a distal end portion 18, and an intermediate portion 20 extending between the proximal and distal end portions. The elongated body member 12 can have a tubular or cylindrical shape; however, it will be appreciated that other ergonomic shapes are possible. In some instances, each of the proximal and distal end portions 16 and 18 can have a tapered configuration (relative to the intermediate portion 20) to assist with handling the treatment probe 10. Although not shown in FIG. 1, the elongated body member 12 can include an internal reservoir for holding a tumescent fluid. Alternatively, the elongated body member 12 can include one or more external fluid lines (not shown) connected to a source of tumescent fluid (not shown). All or only a portion of the elongated body member 12 can be made of a durable material, such as a metal, metal alloy, or a hardened plastic.

Figure 1:
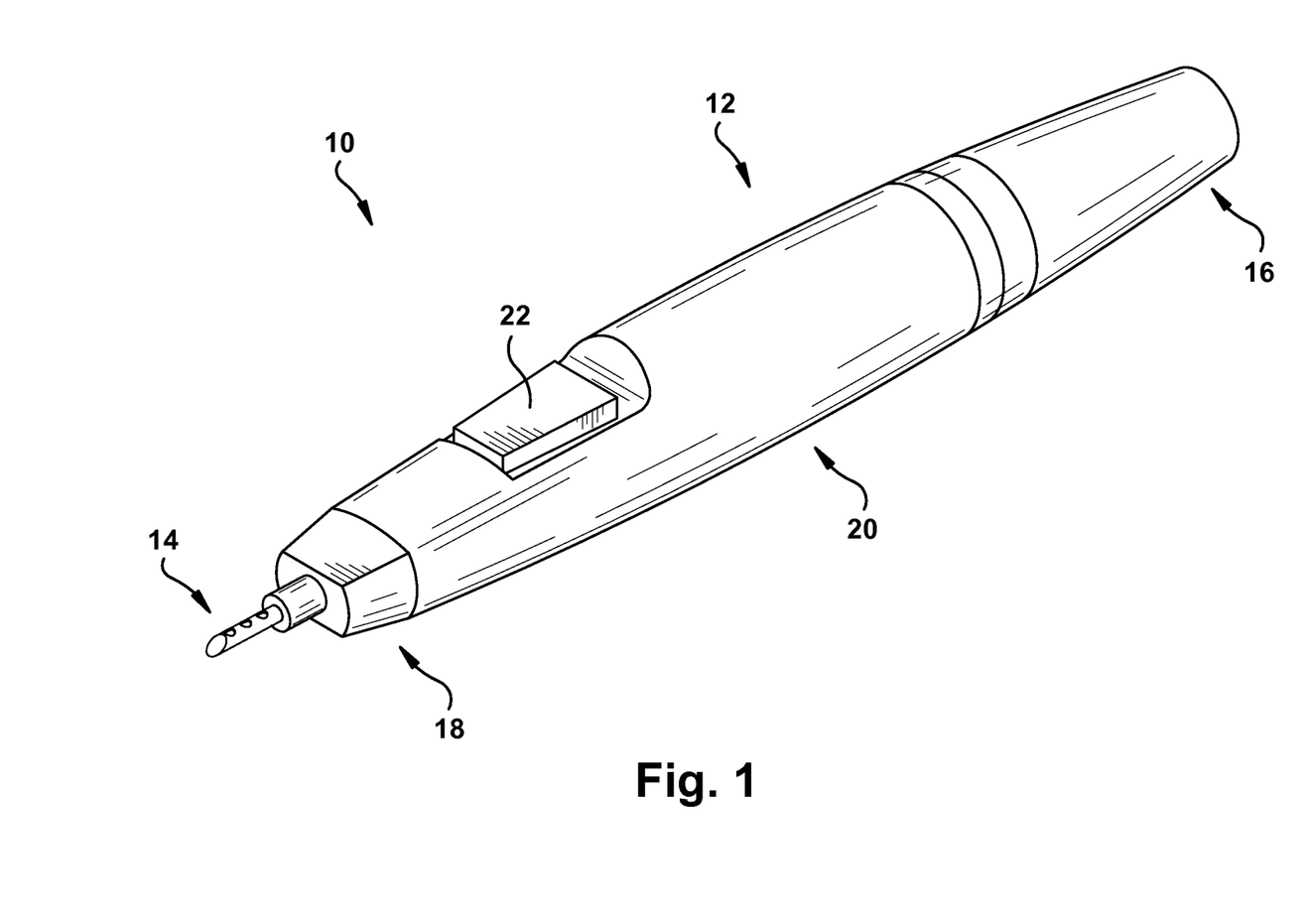
FIG. 1 is a perspective view showing a treatment probe constructed in accordance with one aspect of the present disclosure.

In another aspect, a power button 22 can be operably disposed on the elongated body member 12. Although the power button 22 is shown in FIG. 1 as being disposed on the intermediate portion 20 of the body member 12, it will be appreciated that the power button can be disposed about any other portion of the elongated body member to facilitate use of the treatment probe 10. As described in more detail below, the power button 22 can be used to control one or a combination of functions of the treatment probe 10, such as delivery of electrical energy, flow of a tumescent fluid, aspiration and/or suctioning, and electrical sensing.

Although not shown, a power source can also be associated with the elongated body member 12. The power source can comprise any device capable of generating electrical energy, such as high frequency ultrasound, high energy radiowaves, high frequency electrical stimulation, and laser energy. In some instances, the power source can include a battery housed within the elongated body member 12. In other instances, the power source can be externally coupled to the elongated body member 12. For example, the power source can be electrically connected to the proximal end portion 16 of the elongated body member 12 using an insulated electrical lead or wire (not shown).

Figure 2A:
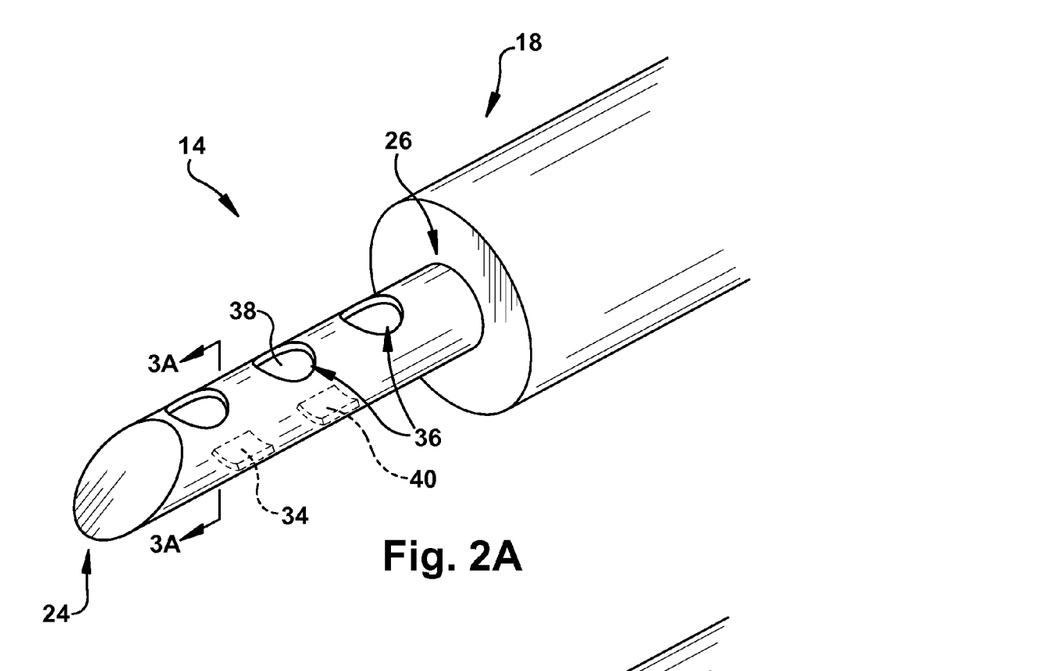
FIGS. 2A-B are magnified perspective views showing a needle portion of the treatment probe in FIG. 1.
Figure 2B:
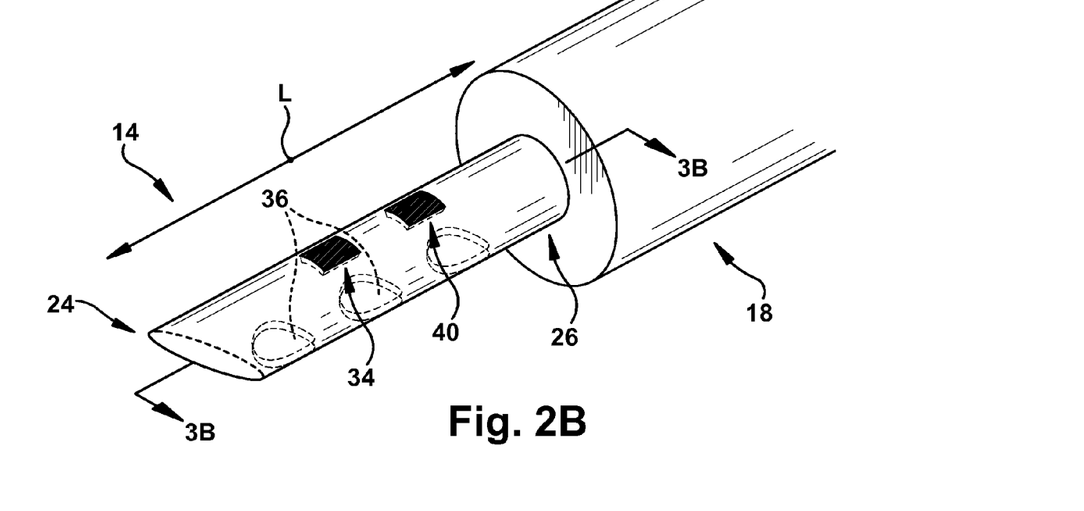

In another aspect, the distal end portion 18 of the elongated body member 12 can be connected (e.g., directly connected) to the needle portion 14. The needle portion 14 can generally comprise a hollow conduit that is shaped and configured to penetrate tissue, such as skin. In some instances, all or only a portion of the needle portion 14 can be comprised of a non-conductive material, such as a hardened plastic. In other instances, the needle portion 14 can be comprised of a metal or metal alloy, such as stainless steel. As shown in FIGS. 2A-B, the needle portion 14 can include an elongated shaft having oppositely disposed distal and proximal ends 24 and 26. The needle portion 14 can also include a channel 28 or lumen, which is defined by an outer surface 30 and an inner surface 32 of the shaft. The channel 28 or lumen can be configured to receive a tumescent fluid. In some instances, the channel 28 or lumen can be in fluid communication with a tumescent fluid reservoir housed within the elongated body member 12. Alternatively, the channel 28 or lumen can be in fluid communication with a fluid line (not shown) that extends through the elongated body member 12 to an external tumescent fluid reservoir.

The needle portion 14 includes a length L, which extends between the distal and proximal ends 24 and 26 of the shaft. The length L of the needle portion 14 can be between about 0.5 cm to about 5 cm, or more, depending upon the intended application of the treatment probe 10. In some instances, the proximal end 26 of the shaft can be directly connected to the proximal end portion 16 of the elongated body member 12. In other instances, the distal end 24 of the shaft can have a tapered and/or sharpened configuration (e.g., a sharpened tip) to facilitate insertion of the needle portion 14 into a subject. Although the shaft is shown as extending axially from the proximal end portion 16 of the elongated body member 12, it will be appreciated that a portion of the shaft (e.g., the distal end 24) may be curved or have an arcuate configuration. The shaft of the needle portion 14 can also include an outer diameter, which corresponds to a conventional needle gauge. Thus, in some instances, the needle portion 14 can comprise a needle (e.g., a hypodermic needle) having a gauge between 7 and 34.

Figure 3A:
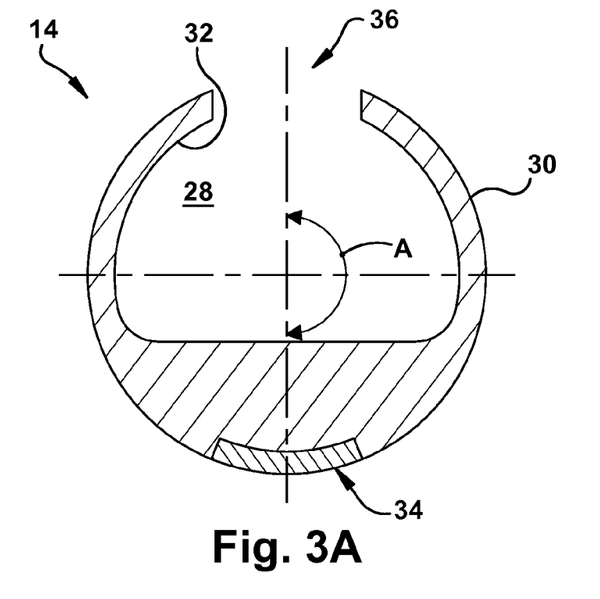
FIG. 3A is a cross-sectional view taken along Line 3A-3A in FIG. 2A.
Figure 3B:
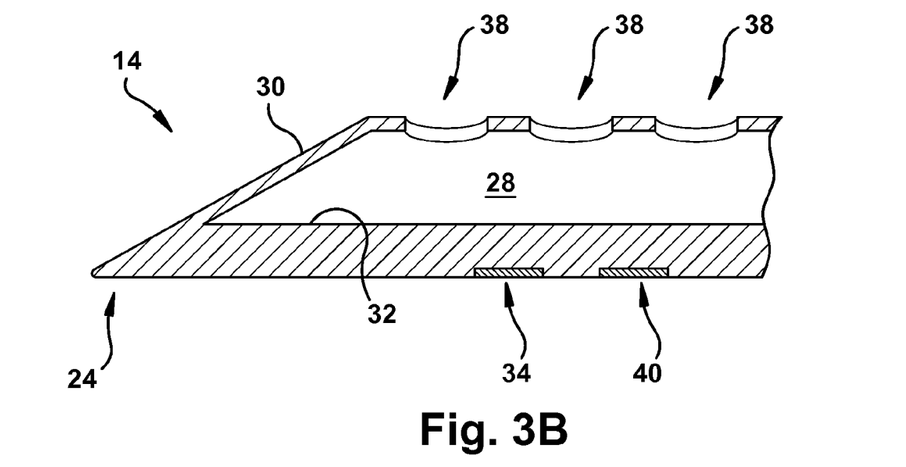
FIG. 3B is a cross-sectional view taken along Line 3B-3B in FIG. 2B.
Figure 4:
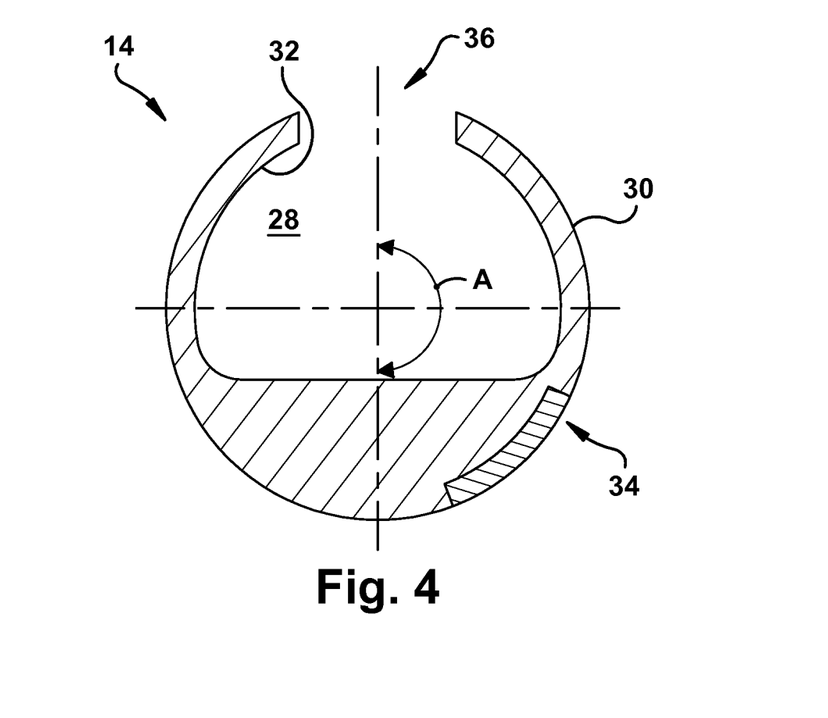
FIG. 4 is a cross-sectional view showing an alternative configuration of the needle portion in FIG. 3A.
Figure 5:
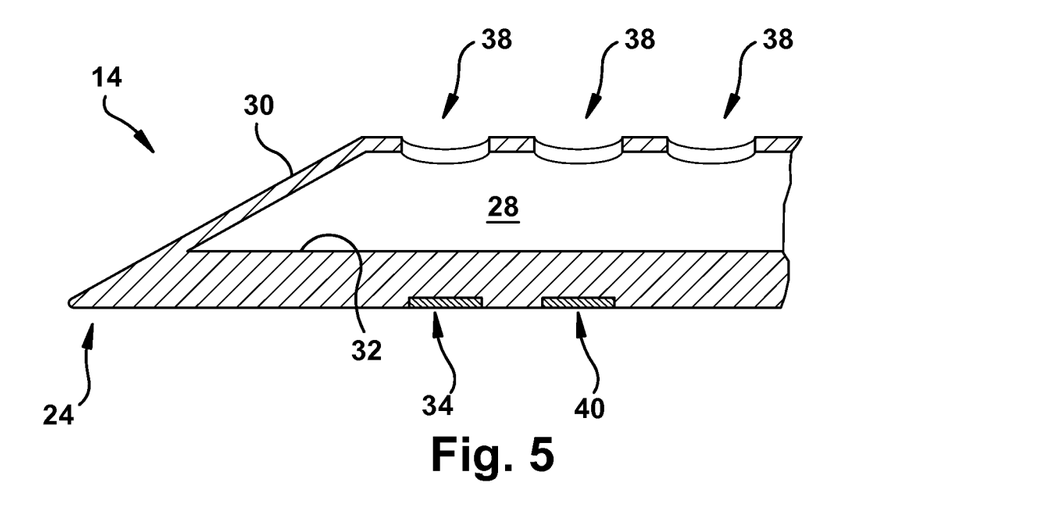
FIG. 5 is a cross-sectional view showing an alternative configuration of the needle portion in FIG. 3B.

In another aspect, the needle portion 14 includes at least one electrode 34 and at least one fluid port 36, which are configured to deliver electrical energy and a tumescent fluid, respectively, so that superficial tissue planes overlying a target nerve are protected from inadvertent heat damage as a result of application of electrical energy to a target nerve. As shown in FIGS. 2A-B, the fluid ports 36 and the electrode 34 are oppositely disposed from one another. The electrode 34 and the fluid ports 36 can be oppositely disposed from one another other by an angle A sufficient to ensure that electrical energy is delivered to a target nerve but not to superficial tissue planes overlying the target nerve. Thus, in some instances, the angle A can range from about 180° to about 90°. A variety of fluid port 36 and electrode 34 configurations are possible, so long as superficial tissue planes overlying a target nerve are protected from inadvertent heat damage as a result of application of electrical energy to a target nerve. As shown in FIGS. 3A-B, for example, the fluid ports 36 can be axially offset from, and radially aligned with, the electrode 34. In another example, the fluid ports 36 can be axially and radially offset from the electrode 34 (FIGS. 4-5).

Each of the fluid ports 36 extends between the outer and inner surfaces 30 and 32 of the shaft, and includes an opening 38 in fluid communication with the channel 28 or lumen.

Although three fluid ports 36 are shown in FIGS. 2A-B, it will be appreciated that the needle portion 14 can include one, two, four, or more fluid ports. The fluid ports 36 can have any desired cross-sectional shape, such as ovoid, circular, square, rectangular, etc. Each of the fluid ports 36 can have the same or different cross-sectional shape. The diameter of each fluid port 36 can be the same or different as compared to the diameter(s) of other fluid port(s). The fluid ports 36 can be equally or asymmetrically spaced apart from one another.

One or more electrodes 34 can be oppositely disposed from the fluid ports 36 such that electrical energy delivered by the electrode(s) is directed away from the flow of tumescent fluid through the fluid ports. The electrode(s) 34 can comprise any one or combination of materials capable of conducting electrical energy, such as platinum, platinum-iridium, stainless steel, gold-plated copper, and the like. Additionally or optionally, at least a portion of each electrode 34 can be embedded within, or coated with, a polymeric material (or other similar material) (e.g., silicone) to protect tissue from abrasion, promote biocompatibility and/or electrical conduction. The electrode(s) 34 can have any desired shape, such as square, ovoid, circular, rectangular, etc. The electrode(s) 34 can have the same shape or, alternatively, each of the electrodes can have a different shape. The electrode(s) 34 can be equally or asymmetrically spaced apart from one another.

In another aspect, the needle portion 14 can include at least one sensing electrode 40 for monitoring or detecting the electrical activity of a target nerve. Similar to the electrode 34, the sensing electrode 40 can be located opposite the fluid ports 36. As shown in FIGS. 2A-B, for example, the sensing electrode 40 can be located proximal to the electrode 34; although, it will be appreciated that the sensing electrode can be located distal to the electrode. The sensing electrode 40 is capable of monitoring a desired metabolic parameter (e.g., electrical activity) associated with a nerve, nervous tissue, and/or muscle function. For example, the sensing electrode 40 can include at least one electromyographic (EMG) electrode capable of receiving a signal from a target nerve or muscle tissue when the sensing electrode is placed in electrical contact with the target nerve or muscle tissue. As explained in more detail below, the sensing electrode 40 can be used to verify that a target nerve is an appropriate target for ablation.

In another aspect, the treatment probe can include a tumescent fluid delivery and/or aspiration mechanism (not shown in detail). In some instances, a tumescent fluid delivery and/or aspiration mechanism can include one or more pumps (not shown) in fluid communication with the channel 28 or lumen of the needle portion 14. For example, the treatment probe 10 can include a pump configured to deliver tumescent fluid through the channel 28 or lumen. Alternatively or additionally, the treatment probe 10 can include the same or a different pump for suctioning fluid (e.g., blood, tumescent fluid, etc.) from the area surrounding a target nerve. In some instances, a pump (or pumps) can be disposed within the elongated body member 12 or, alternatively, a pump (or pumps) can be located externally from the treatment probe 10. Operation of the fluid delivery and/or aspiration mechanism can be controlled by the power button 22.

Methods

Figure 6:
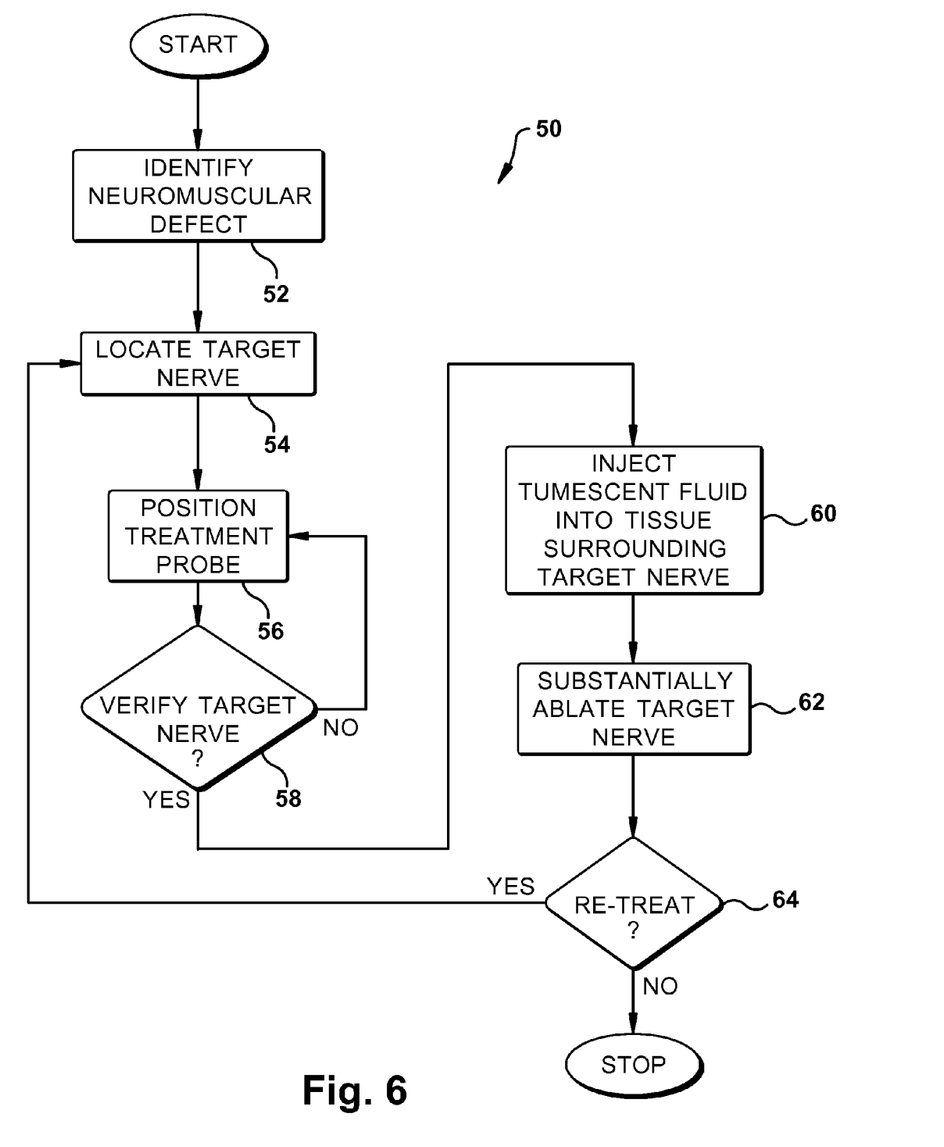
FIG. 6 is a process flow diagram illustrating a method for treating a neuromuscular defect in a subject according to another aspect of the present disclosure.

Another aspect of the present disclosure can include a method 50 (FIG. 6) for treating a neuromuscular defect or neuromuscular junction disorder in a subject. At Step 52, the method 50 can include identifying a neuromuscular defect in the subject. Generally, the neuromuscular defect can include any disease, disorder, or condition that adversely affects both nervous elements (e.g., brain, spinal cord, peripheral nerve) and muscle (e.g., striated or smooth). Non-limiting examples of neuromuscular defects can include cosmetic defects, neurological movement disorders, neuromuscular pain, and headaches.

Non-limiting examples of cosmetic defects can include frown lines, lines or wrinkles between the eyes 66 (FIG. 7), crow's feet, horizontal lines in the forehead and neck, wrinkles around the mouth and chin, skin furrows, contractions in the face and neck, spasms in the face or neck, and neck bands.

Neurological movement disorders can include any neurological disease or condition that affects the speed, fluency, quality, and/or ease of movement in a subject. For example, abnormal fluency or speed of movement (dyskinesia) may involve excessive or involuntary movement (hyperkinesia) or slowed or absent voluntary movement (hypokinesia). Examples of neurological movement disorders can include, but are not limited to, dystonias, torticollis, bleharospasm, and uncontrolled grimacing.

Non-limiting examples of neuromuscular pain can include myofascial pain, fibromyalgia, TMJ pain, carpal tunnel syndrome, pain associated with muscular dystrophy, orofacial pain, chronic head and neck pain, and pain associated with herniated and/or bulging or ruptured vertebral discs. Myofascial pain can involve any one or combination of nerves that supply the face or, alternatively, indirect (referred) pain from other structures in the head, e.g., blood vessels. Myofascial pain may be related to headache (e.g., migraine), muscular syndromes, such as TMJ, and herpetic or rheumatic disease or injury.

Non-limiting examples of headaches can include migraines, tension headaches, cluster headaches, trigeminal neuralgia, secondary headaches, and miscellaneous-type headaches. Migraines can include intense and disabling episodic headaches typically characterized by severe pain in one or both sides of the head. For example, migraines can include migraine without aura, migraine with aura, and migraine with aura but without headache. Cluster headaches can include extremely painful and debilitating headaches that occur in groups or clusters. For example, cluster headaches can include cluster-type headaches, histamine headaches, histamine cephalalgia, Raedar's syndrome, and sphenopalatine neuralgia.

Figure 7:
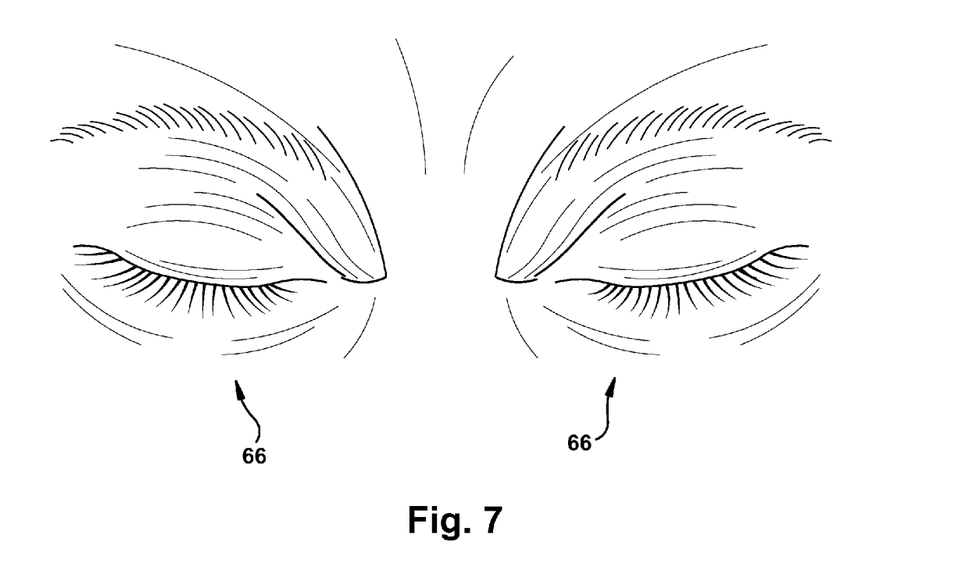
FIG. 7 is a schematic illustration of a subject's orbital region showing uncontrolled blinking or blepharospasm.

To identify the neuromuscular defect, a subject is monitored for one or more observable clinical symptoms associated with a particular neuromuscular defect. As shown in FIG. 7, for example, a subject suffering from blepharospasm may exhibit involuntary and sustained muscle contractions of the muscles around the eyes 66. Alternatively, symptoms associated with a particular neuromuscular defect may not be clinically observable. In this case, the subject may be asked to report his or her symptom(s) associated with the particular neuromuscular defect. For example, the subject may report the sensation of facial or head pain associated with a headache.

After the neuromuscular defect has been identified, a target nerve can be located at Step 54. Generally, the target nerve can include any portion of a subject's nervous system that has been identified to benefit from receiving electric current based on the identified neuromuscular defect. Examples of target nerves in the face of a subject, as well as the muscles innervated by the target nerves are illustrated in FIG. 8. It should be appreciated, however, that other target nerves, such as those of the peripheral nervous system may also be targeted by the method 50.

Referring to FIG. 8, the facial nerve 68 is the motor nerve that controls a significant portion of the muscles responsible for facial expressions. The branches of the facial nerve 68 pass around and through superficial facial and neck muscles to control the corrugator supercilii muscle 70, the procerus muscle 72, and the platysma myoides muscle 74, among many others. The facial nerve 68 is the seventh cranial nerve, which is part of the peripheral nervous system of the body. Disorders or defects in facial nerve 68 function can cause various cosmetic defects, such as blepharospasm. Thus, the facial nerve 68 and/or one of its branches can be an appropriate target nerve for treating a subject suffering from blepharospasm.

The corrugator supercilii 70 is a small and narrow pyramidal muscle. The corrugator supercilii 70 is located at the inner extremity of the eyebrow beneath the orbicularis palpebrarum muscle 76. As FIG. 8 shows, the temporal branch 78 of the facial nerve 68 provides additional nerve branches 80 to the corrugator supercilii muscle 70. The corrugator supercilii muscle 70 is called the "frowning muscle" because it draws the eyebrows downward and inward, producing vertical wrinkles in the forehead and in the space between the eyebrows.

The procerus 72 is a small, pyramidal band of muscles located over the nasal bone between the eyebrows. The zygomatico-buccal branch (not shown in detail) of the facial nerve 68 supplies the procerus muscle 72. The procerus muscle 72 draws down the inner angle of the eyebrows and produces transverse wrinkles over the bridge of the nose.

The platysma myoides 74 is a broad, thin plane of muscular fibers located immediately beneath the superficial fascia on each side of the neck. The cervical branch (not shown in detail) of the facial nerve 68 supplies the platysma myoides muscle 74. The platysma myoides muscle 74 produces a wrinkling of the surface of the skin of the neck, in an oblique direction, when the entire muscle is brought into action. It also serves to draw down the lower lip and angle of the mouth on each side.

A neuromuscular defect can lead to uncontrolled contraction of one or more of the corrugator supercilii 70, the procerus 72, and the platysma myoides 74 muscles. Uncontrolled contraction of the corrugator supercilii muscle 70 or the procerus muscle 72, for example, can continuously contract the brow, giving the outward appearance of displeasure or disapproval even in the absence of the corresponding emotional state. Likewise, uncontrolled contraction of the platysma myoides muscle 74 (called torticollis) can lead to sudden neck movement. Repeated normal contraction of the platysma myoides muscles 74 can also lead to the formation of aesthetically displeasing bands in the skin area below the neck over time. Even without hyperfunctional dysfunction, normal contraction of these muscles can, over time, cause aesthetically displeasing frown lines or furrows in the forehead or in the space between the eyebrows. Additionally, exposure to the sun can accelerate this wrinkling process.

At Step 56, a treatment probe 10 can be positioned about a target nerve. Any one or combination of approaches can be used to access the target nerve with the treatment probe 10. For example, the needle portion 14 of the treatment probe 10 can be inserted directly through the skin adjacent a target nerve or, alternatively, an incision 82 (FIG. 9) can be made in the skin adjacent the target nerve. The needle portion 14 can be positioned so that at least one electrode 34 and/or at least one sensing electrode 40 is/are in electrical communication with the target nerve. For example, the needle portion 14 can be oriented so that at least one electrode 34 is directly adjacent the target nerve. In other instances, the needle portion 14 of the treatment probe 10 is urged through the incision 82 so that the distal end 24 of the needle portion, and in particular the electrode 34, is in electrical contact with the target nerve. By "electrical contact" it is meant that when electric current is delivered to the electrode 34, deplorization of at least one neuron comprising the target nerve is elicited.

Figure 9:
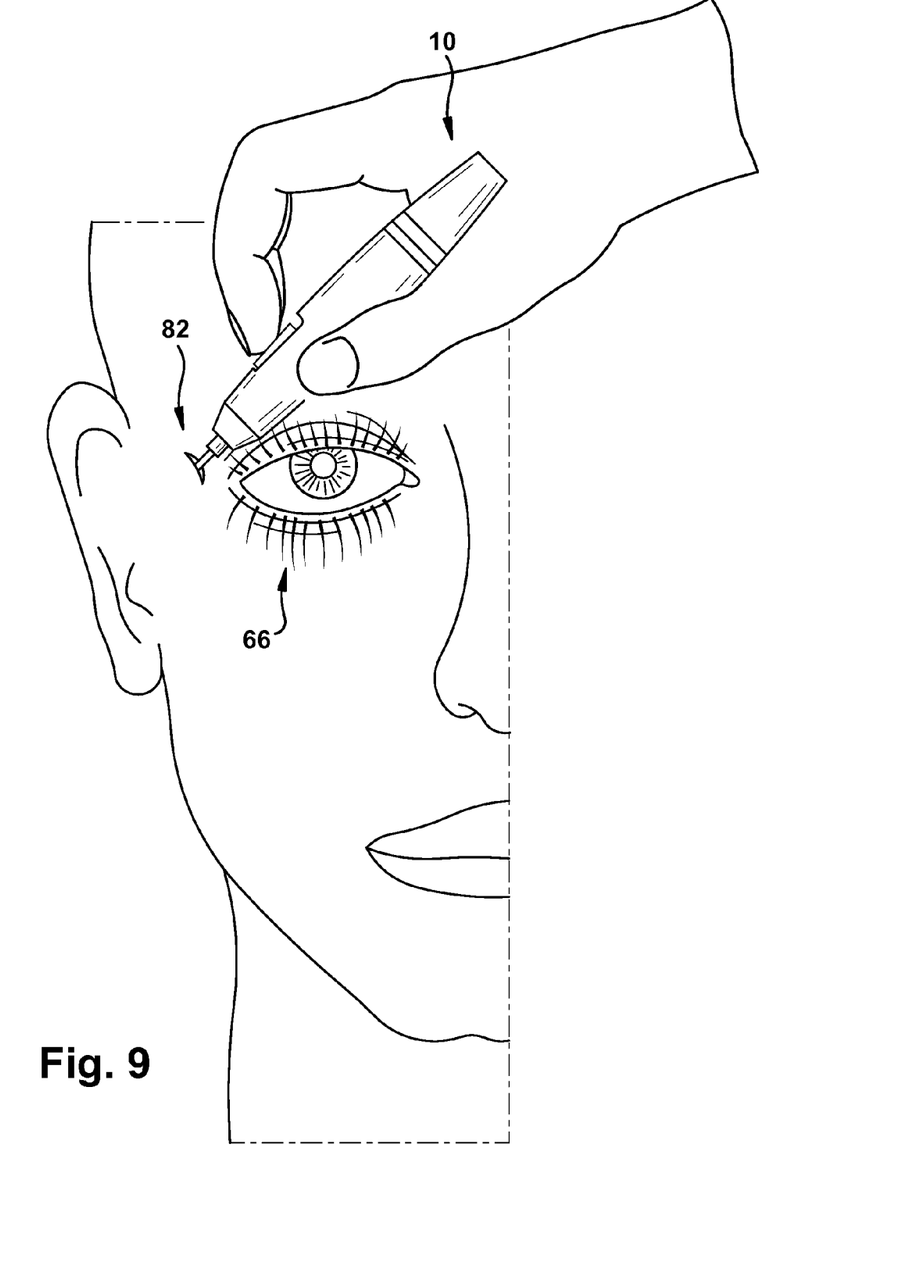
FIG. 9 is a perspective view showing the distal end portion of the treatment probe in FIG. 1 being positioned about a target nerve.

In a subject suffering from blepharospasm, for example, an incision 82 can be made near the right corner of a subject's eye 66 using a scalpel (not shown). In this case, the incision 82 should be made so that a portion of the facial nerve 68 and/or one of its branches is sufficiently exposed to facilitate accurate placement of the treatment probe 10. As shown in FIG. 9, for example, the needle portion 14 of the treatment probe 10 can be inserted into the incision 82 so that the electrode 34 is adjacent a portion of the facial nerve 68 and/or one of its branches. As discussed in more detail below, the position of the electrode 34 relative to the target nerve can be adjusted using the sensing electrode 40 during placement of the treatment probe 10. For example, the position of the electrode 34 can be adjusted based on sensed electrical patterns in the target nerve and/or tissue surrounding the target nerve using EMG mapping.

Following placement of the needle portion 14, a determination is made as to whether the target nerve is appropriate for ablation at Step 58. To verify whether the target nerve is appropriate for ablation, electric current is delivered to the electrode 34. Electric current can be delivered to the electrode 34 continuously, periodically, episodically, or a combination thereof. For example, electric current can be delivered in a unipolar, bipolar, and/or multipolar sequence or, alternatively, via a sequential wave, charge-balanced biphasic square wave, sine wave, or any combination thereof. Electric current can be delivered all at once or, where the needle portion 14 includes two or more electrodes 34, electric current can be delivered to only one of the electrodes using a controller (not shown) and/or known complex practice, such as current steering.

The particular voltage, current, and frequency delivered to the electrode 34 may be varied as needed. For example, electric current can be delivered to the electrode 34 at a constant voltage (e.g., at about 0.1 v to about 25 v), at a constant current (e.g., at about 25 microampes to about 50 milliamps), at a constant frequency (e.g., at about 5 Hz to about 10,000 Hz), and at a constant pulse-width (e.g., at about 50 μsec to about 10,000 μsec).

Delivery of electric current to the electrode 34 stimulates the target nerve, i.e., causes the target nerve to increase the frequency of nerve impulses. Depending upon the anatomical structure(s) and/or other nerve pathways innervated by the target nerve, a measurable result indicative of the appropriate target nerve can be determined by the sensing electrode 40 upon delivery of electric current. In a subject suffering from headache, for example, the measurable result may include some degree of pain relief. Alternatively, in a subject suffering from blepharospasm, the measurable result may include a reduction in uncontrolled blinking. If an appropriate measurable result is not observed upon delivery of electric current, the needle portion 14 can be re-positioned, electric current again delivered to the electrode 34, and a measurable result then observed.

Figure 10:
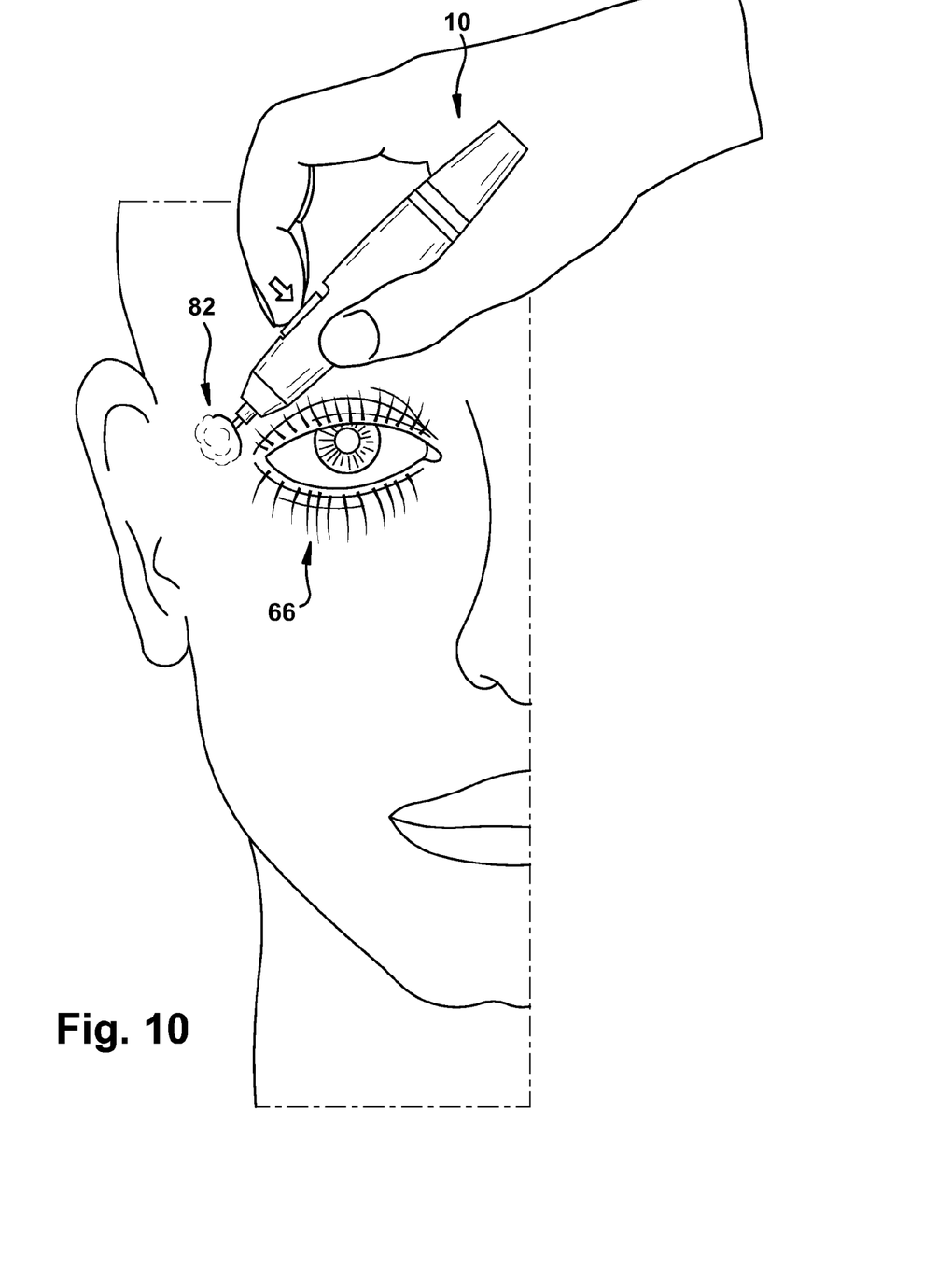
FIG. 10 is a perspective view showing the treatment probe in FIG. 9 being used to deliver a tumescent fluid to the tissue surrounding the target nerve.

At Step 60, an appropriate volume of a tumescent fluid can be injected into the tissue surrounding the target nerve (FIG. 10). For example, the tumescent fluid can be delivered to the tissue surrounding the target nerve by flowing the tumescent fluid through the fluid ports 36 so that the flow of tumescent fluid is directed away from the target nerve. The tumescent fluid can be stored in the treatment probe 10 or, alternatively, supplied from an external fluid source (not shown). The tumescent fluid can comprise any solution capable of protecting superficial tissue planes from inadvertent heat damage and enhancing electro-mechanical condition during delivery of electric current to the target nerve. For example, the tumescent fluid can comprise sterile water or an electrolyte solution (e.g., a physiologically normal saline solution).

Depending upon the particular neuromuscular defect being treated, the tumescent fluid can also include at least one pharmacological agent. Non-limiting examples of pharmacological agents can include anesthetic agents, such as lidocaine, marcaine, nesacaine, diprivan, novocaine, ketalar and xylocaine, vasoconstrictive agents, such as epinephrine, levarterenol, phenylephrine, athyladrianol and ephedrine, anti-inflammatory agents, such as free radical scavengers and anti-oxidants (e.g., superoxide dismutase, catalase, nitric oxide, mannitol, allopurinol, and dimethyl sulfoxide), NSAIDS (e.g., aspirin, acetaminophen, indomethacin and ibuprofen), steroidal agents (e.g., glucocorticoids and hormes), calcium channel blockers (e.g., nimodipine, nifedipine, verapamil and nicardipine), NMDA antagonists (e.g., magnesium sulfate and dextromethorphan), and neurotoxic agents, such as Botulinum toxin.

Figure 11A:
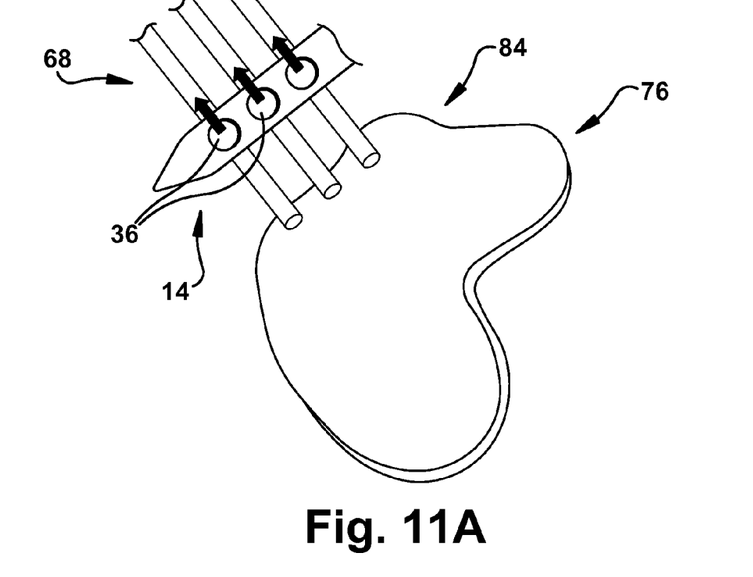
FIG. 11A is a perspective view showing a neuromuscular junction located between a target nerve and a muscle.

After an appropriate volume of tumescent fluid has been injected into the tissue surrounding the target nerve, the target nerve can be substantially ablated at Step 62. To substantially ablate the target nerve, the electrode 34 can be positioned adjacent or directly adjacent a portion of the contractile chain comprising the target nerve. The contractile chain comprises nerve tissue (e.g., a neuron), a neuromuscular junction 84 (FIG. 11A) (which generally forms the interface between nerves and muscles), muscle tissue, and connective tissue. As shown in FIG. 11A, for example, the electrode 34 can be positioned substantially adjacent a neuromuscular junction 84. Although, it will be appreciated that the electrode 34 can be positioned directly adjacent a neuromuscular junction 84.

Muscular movement is generally controlled by stimulation of a nerve. The motor unit of the neuromuscular system contains three components: motor neuron (spine), axon (spine to motor endplate), and innervated muscle fibers (endplate to muscle). Each muscle receives one or more supply nerves, and the supply nerve generally enters deep into the muscle surface near its origin where the muscle is relatively immobile. Often times, blood vessels can accompany the nerve to enter the muscle at the neurovascular hilum. Each nerve contains motor and sensory fibers, motor endplates, vascular smooth muscle cells, and various sensory endings and endings in fascia. When the nerve enters the muscle, it breaks off into a plexus running into the various layers of muscle epimysium, perimysium and endomysium, each terminating in several branches joining a muscle fiber at the motor endplate.

Substantially ablating one or more of these tissues may be sufficient to temporarily or permanently inhibit (or substantially block) muscle contraction. Substantially ablating a target nerve may interrupt or disable nerve impulses by disrupting conductivity, and thereby blocking or substantially blocking nerve activity. Disruptions in nerve conductivity may be caused by eliminating or decreasing charge differences across plasma membranes, either mechanically or chemically, destroying Schwann cells that insulate the axonal processes, repeated injury/healing cycles timed to limited capacity for neuron regeneration, or a combination thereof.

The electrode 34 can be brought into direct or indirect contact with the target nerve. By "direct" it is meant that the electrode 34 is brought into physical contact with the target nerve. By "indirect" it is meant that the electrode 34 is positioned about the target nerve without directly contacting the target nerve, such that delivery of electric current to the electrode can modulate activity of the target nerve. Regardless of the specific component of the contractile chain which is substantially ablated, delivery of electric current to the target nerve can inhibit contraction of a muscle that would otherwise form or cause the neuromuscular defect.

Substantial ablation of the target nerve is accomplished when electric current is delivered to the electrode 34 via the power source. The parameters for delivery of electric current to the electrode 34 can be identical or similar to the parameters described above. For example, electric current can be delivered to the electrode 34 at a constant voltage (e.g., at about 0.1 v to about 25 v), at a constant current (e.g., at about 25 microampes to about 50 milliamps), at a constant frequency (e.g., at about 5 Hz to about 10,000 Hz), and at a constant pulse-width (e.g., at about 50 μsec to about 10,000 μsec).

Figure 11B:
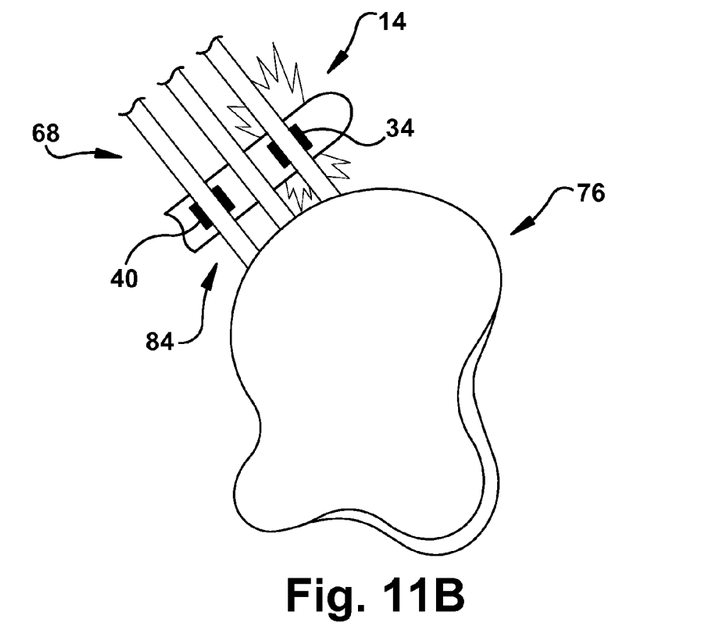
FIG. 11B is a perspective view showing the needle portion of the treatment probe in FIG. 1 being used to substantially ablate the target nerve.

As shown in FIG. 11B, delivery of electric current to the electrode 34 can substantially ablate a neuromuscular junction 84 comprising an end of a facial nerve 68 (or branch thereof) and the orbicularis palpebrarum muscle 76, for example. Such ablation may result in a short-term, long-term, or permanent inactivation of the muscle. Other long-lasting or permanent treatments may involve inducing apoptosis to remodel the tissue behavior with long-term changes in the cellular life and/or proliferation cycles.

Specific ablative approaches used to change the function of a target nerve and its corresponding muscle(s) in a desired way, or for a desired time, may be induced by appropriate delivery of electric current to the electrode 34. Alternative ablative approaches that may be shorter in effect can include, for example, stunning of one or more components of contractile chain or inactivating one or more of the components. Ablative approaches that effectively block the release of, or response to, chemicals (e.g., neurotransmitters) along the contractile chain may also be sufficient to inhibit (e.g., temporarily or permanently) muscular contraction in response to signals transmitted along the neural pathways.

Figure 12:
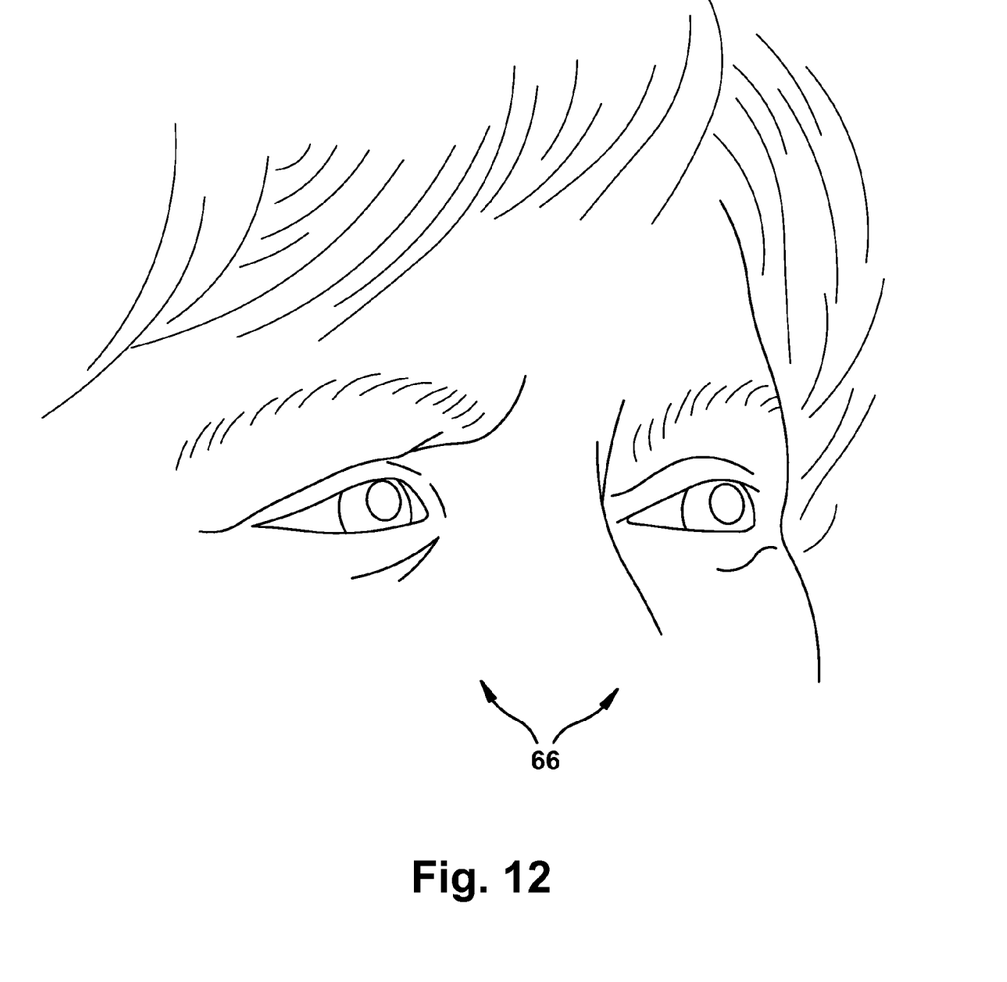
FIG. 12 is a schematic illustration showing the subject in FIG. 7 after being treated for blepharospasm according to the present disclosure.

After substantially ablating the target nerve, the subject can be re-assessed to determine if the method 50 was effective in treating the neuromuscular defect. In a subject suffering from blepharospasm, for example, a medical practitioner or other health care professional can observe the subject for uncontrolled blinking. Depending upon the observed result, the method 50 can be repeated at Step 64. If the subject exhibits normal blinking (FIG. 12), for example, no additional treatment may be needed. Where no additional treatment is needed, the incision 82 or entry point used to access the target nerve can be sutured or bandaged and the method 50 completed.

Although not illustrated in FIGS. 6-12, it should be appreciated that the method 50 can be targeted to any one or combination of the nerves or muscles identified in FIG. 8 to treat a variety of cosmetic defects other than blepharospasm. For example, the method 50 may be directed towards one or more of the levator palpebrae superioris, the frontalis, the levator labii, the corrugator supercilii 70, the zygomaticus minor, the zygomaticus major, the buccinator, and/or the temporalis. Treatments targeting contraction of the oticularis may help decrease crow's feet wrinkles, while treatments altering the function of the frontalis may alleviate wrinkles. Additionally, wrinkles of the chin may be mitigated by treatment of the mentali, and neck wrinkles may be improved by treatment of the platysma 74.

Other examples of muscles whose innervating nerve(s) may be substantially ablated to alleviate a cosmetic defect (or defects) can include the glabellar and procerus complex, the nasalis, the depressor anguli oris, the quadratus labii superioris and inferioris, the zygomaticus, the maxillae, the frontalis pars medialis, the frontalis pars lateralis, the levator palpebrae superioris, the orbicularis oculi pars orbitalis, the orbicularis oculi pars palpebralis, the levator labii superioris alaquae nasi, the levator labii superioris, the zygomaticus minor, the zygomaticus major, the levator anguli oris (a.k.a. caninus), the depressor anguli oris (a.k.a. triangularis), the depressor labii inferioris, the mentalis, the incisivii labii superioris, the incisivii labii inferioris, the risorius, the masseter, the internal pterygoid, the digastric, the maxillae, and the quadratus labii superioris and inferioris. Contraction of these and/or other muscles may be inhibited by targeting associated nervous tissue(s), connective tissue(s), nerve/muscle interface(s), blood supply, or a combination thereof.

From the above description of the invention, those skilled in the art will perceive improvements, changes and modifications. Such improvements, changes, and modifications are within the skill of the art and are intended to be covered by the appended claims.

The following is claimed:

1. A treatment probe comprising:
   an elongated body member having a proximal end portion and a distal end portion; and
   a needle portion connected to said distal end portion, said needle portion including at least one electrode and at least one fluid port, said at least one electrode and said at least one fluid port being configured to deliver electrical energy and a tumescent fluid, respectively, so that the electrical energy is delivered to the target nerve, but not to superficial tissue planes overlying the target nerve, and the superficial tissue planes overlying a target nerve are protected from inadvertent heat damage as a result of application of electrical energy to a target nerve, said at least one electrode being disposed on an outer surface of said needle portion and located opposite said at least one fluid port;
   wherein said needle portion includes an elongated shaft having a closed, sharpened distal end;
   wherein said at least one fluid port is configured to deliver a tumescent fluid flow away from the target nerve;
   wherein electrical energy delivered by said at least one electrode is directed away from the flow of tumescent fluid through said at least one fluid port;
   wherein said needle portion further includes at least one sensing electrode that is axially spaced apart from said at least one electrode.

2. The treatment probe of claim 1, wherein said at least one electrode and said at least one fluid port are radially offset from one another.

3. The treatment probe of claim 1, wherein said at least one electrode and said at least one fluid port are radially aligned with one another.

4. The treatment probe of claim 1, wherein said at least one electrode and said at least one fluid port are axially offset from one another.

5. The treatment probe of claim 1, wherein said body member includes a power button disposed thereon.

6. The treatment probe of claim 1, wherein the tumescent fluid is stored within said body member.

7. The treatment probe of claim 1, wherein said shaft of said needle portion further comprises:
   an inner circumferential surface; and
   an outer circumferential surface;
   wherein said at least one fluid port extends between said inner and outer circumferential surfaces to form an opening in fluid communication with a channel that extends through said needle portion.

8. The treatment probe of claim 1, further comprising a power source that is housed within said elongated body member so that said treatment probe is free from connection with an external power source.

9. The treatment probe of claim 1, wherein the at least one sensing electrode that is disposed on an outer surface of said needle portion and opposite of said at least one fluid port.

10. The treatment probe of claim 1, further comprising a fluid aspiration and delivery mechanism in fluid communication with a channel of said needle portion.

11. A treatment probe comprising:
    an elongated body member having a proximal end portion and a distal end portion; and
    a needle portion connected to said distal end portion, said needle portion including at least one electrode and at least one fluid port, said at least one electrode and said at least one fluid port being configured to deliver electrical energy and a tumescent fluid, respectively, so that the electrical energy is delivered to the target nerve, but not to superficial tissue planes overlying the target nerve, and the superficial tissue planes overlying a target nerve are protected from inadvertent heat damage as a result of application of electrical energy to a target nerve, said at least one electrode being disposed on an outer surface of said needle portion and located opposite said at least one fluid port; and
    a power source that is housed within said elongated body member so that said treatment probe is free from connection with an external power source;
    wherein said needle portion includes an elongated shaft having a closed, sharpened distal end;
    wherein said at least one fluid port is configured to deliver a tumescent fluid flow away from the target nerve;
    wherein electrical energy delivered by said at least one electrode is directed away from the flow of tumescent fluid through said at least one fluid port.

12. A treatment probe comprising:
    an elongated body member having a proximal end portion and a distal end portion; and
    a needle portion connected to said distal end portion, said needle portion including at least one electrode and at least one fluid port, said at least one electrode and said at least one fluid port being configured to deliver electrical energy and a tumescent fluid, respectively, so that the electrical energy is delivered to the target nerve, but not to superficial tissue planes overlying the target nerve, and the superficial tissue planes overlying a target nerve are protected from inadvertent heat damage as a result of application of electrical energy to a target nerve, said at least one electrode being disposed on an outer surface of said needle portion and located opposite said at least one fluid port;
    wherein said needle portion includes an elongated shaft having a closed, sharpened distal end;
    wherein said at least one fluid port is configured to deliver a tumescent fluid flow away from the target nerve;
    wherein electrical energy delivered by said at least one electrode is directed away from the flow of tumescent fluid through said at least one fluid port;
    wherein the tumescent fluid is stored within said body member.

* * * * *